United States Patent
Eftink et al.

(10) Patent No.: US 10,356,391 B1
(45) Date of Patent: Jul. 16, 2019

(54) COMPUTER GENERATED THREE-DIMENSIONAL MODELS OF MICROSTRUCTURAL FEATURES BASED ON STEREOMICROSCOPY

(71) Applicant: Triad National Security, LLC, Los Alamos, NM (US)

(72) Inventors: Benjamin P. Eftink, Santa Fe, NM (US); Stuart Andrew Maloy, Albuquerque, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 15/986,796

(22) Filed: May 22, 2018

Related U.S. Application Data

(60) Provisional application No. 62/519,357, filed on Jun. 14, 2017.

(51) Int. Cl.
| | |
|---|---|
| *H04N 13/00* | (2018.01) |
| *H04N 13/207* | (2018.01) |
| *G06T 7/73* | (2017.01) |
| *H01J 37/244* | (2006.01) |
| *H01J 37/20* | (2006.01) |
| *H01J 37/22* | (2006.01) |

(52) U.S. Cl.
CPC ............ *H04N 13/207* (2018.05); *G06T 7/74* (2017.01); *H01J 37/20* (2013.01); *H01J 37/222* (2013.01); *H01J 37/244* (2013.01); H01J 2237/20207 (2013.01); H01J 2237/2802 (2013.01)

(58) Field of Classification Search
CPC . H04N 13/00; H01L 21/00; G06T 7/00; H01J 37/00
See application file for complete search history.

(56) References Cited

U.S. PATENT DOCUMENTS

2005/0042781 A1* 2/2005 Ogawa .................. G01N 23/04 438/14

* cited by examiner

*Primary Examiner* — Maryam A Nasri
(74) *Attorney, Agent, or Firm* — LeonardPatel PC; Sheetal S. Patel; Michael A. Leonard, II

(57) ABSTRACT

3D information may be extracted from two 2D images by capturing a first image of a sample at a first orientation. The sample may be titled at a second or different orientation, resulting in a second image of the titled sample to be captured. Third dimension of information may be extracted from the images.

18 Claims, 8 Drawing Sheets

COMPUTER GENERATED THREE-DIMENSIONAL MODELS OF MICROSTRUCTURAL FEATURES BASED ON STEREOMICROSCOPY

CROSS-REFERENCE TO RELATED APPLICATION

This application claims the benefit of U.S. Provisional Patent Application No. 62/519,357 filed Jun. 14, 2017. The subject matter of this earlier filed application is hereby incorporated by reference in its entirety.

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD

The present invention generally relates to a method for extracting three-dimensional (3D) information from two two-dimensional (2D) images.

BACKGROUND

There are several methods to extract three-dimensional (3D) information out of collections of two-dimensional (2D) transmission electron micrographs. These include stereograms, weighted back projection (WBP), and simultaneous iterative reconstruction technique (SIRT) methods. There are several applications for extracting the third dimension from transmission electron micrographs, some of which are 3D characterization of dislocations, second phases and irradiation defects. One of the limitations to using weighted back projection or SIRT, is that the quality of the tomogram is related to the range of the tilt and the tilt increment between images. Larger tilt ranges and smaller tilt increments produce higher quality tomograms. Acquiring a series of images with a 70° tilt range with 1° tilt increments, which is typical, limits the application of the technique due to the time-consuming nature.

There are methods employed to reduce the number of images required to produce a tomogram using WBP or SIRT. For example, fiducial markers may be placed on the image at positions of features (for example, where the dislocations end at the surfaces of the foil) which aids the alignment of the images in the reconstruction software. By using this method, tomograms may be constructed using as few as 15 images and have enabled tomograms to be constructed at several stages during an in situ straining experiment in 304 stainless steel.

Even at 15 images, the acquisition process is time consuming. Another significant drawback to conventional electron tomographic methods during in situ straining experiments is that the image contrast should be held constant through the series of images acquired and deviations in contrast such as those found in images near a zone-axis in crystalline samples should not be used. In situ strain transmission electron microscopy (TEM) stages almost exclusively have a single axis of specimen tilt with few exceptions, maintaining the same imaging conditions in crystalline samples for a necessary range of tilt is not likely.

Stereomicroscopy for TEM gets around the necessity of acquiring tens of images, and instead uses 2 images. Interpretation is done by creating an anaglyph or using a stereoviewer, which still requires the two images to be at the same diffraction conditions if the sample is crystalline. Extracting the 3D information is possible using the basis behind stereomicroscopy, the parallax, however, the process previously was tedious.

Accordingly, an improved 3D visualization software method may be beneficial.

SUMMARY

Certain embodiments of the present invention may provide solutions to the problems and needs in the art that have not yet been fully identified, appreciated, or solved by conventional fluence estimators. For example, some embodiments pertain to extracting 3D information from two 2D images.

In an embodiment, a process for extracting 3D information from two 2D images may include capturing a first image of a sample at a first orientation. The process also includes capturing a second image at a different orientation, which may be achieved by tilting the sample. The process further includes extracting a third dimension of information from the first and second images.

In another embodiment, a computer program for extracting 3D information from two 2D images is embodied on a non-transitory medium. The computer program, when executed by at least one processor, is configured to cause an apparatus to capture a first image of a sample at a first orientation, and capture a second image at a different orientation, which may be achieved by tilting the sample. The computer program may also cause the apparatus to extract a third dimension of information from the first and second image.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Some embodiments generally pertain to a method and application for extracting three-dimensional (3D) data from two TEM (or other transmission imaging techniques) images and the aid of computer calculations. This method may determine the 3D coordinates of points, such as locations along dislocations, irradiation defects, and centers of cavities, as well as locations where interfaces meet the TEM foil surface. In certain embodiments, crystallographic information including dislocation line directions and slip planes, interface plane normal, and the orientation relationship between two crystals is presented. Some embodiments may also be applied to chemical maps acquired using scanning TEM with x-ray or electron energy loss spectroscopy techniques. Crystallographic information requires the additional input of two diffraction vectors from one or two diffraction patterns for a single crystal beyond the two images necessary for the 3D model. By using two images, the acquisition times for the data set is reduced, enabling the combination of in situ experiments such as straining or heating while acquiring 3D information. With the assistance of a computer code, the calculations of the 3D information can be done quickly.

Figure 1:
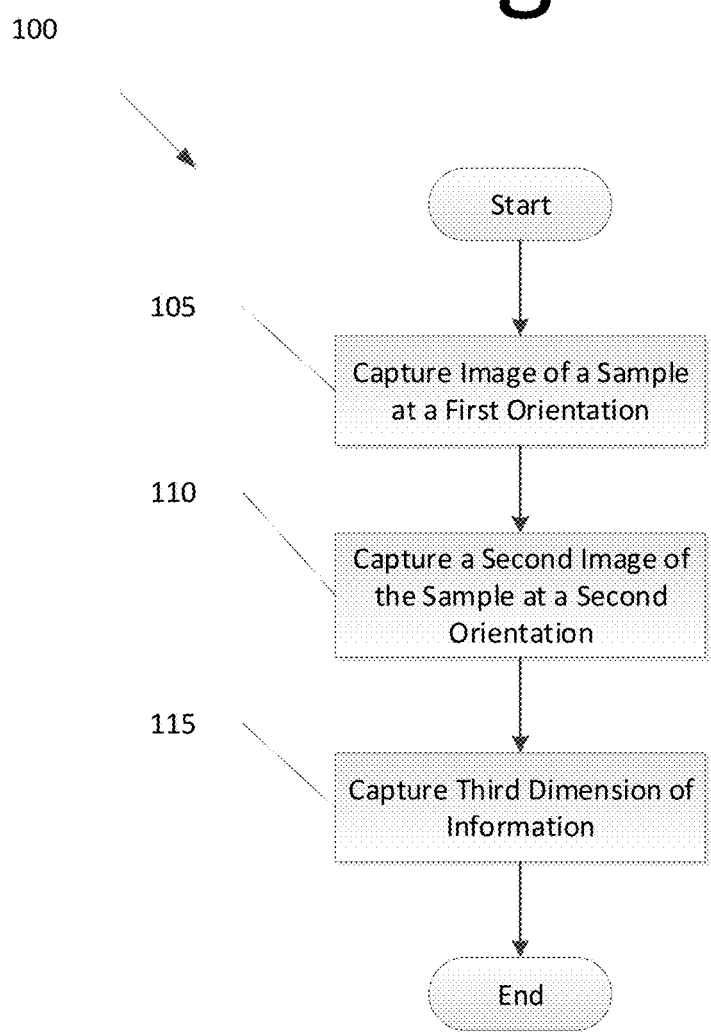
FIG. 1 is a flow diagram illustrating a process for extracting 3D information from a 2D image, according to an embodiment of the present invention.

Simply put, 3D information may be extracted with two 2D images captured at different orientations. Embodiments of the present invention extract the 3D information to create 3D representations of the 2D image. FIG. 1 is a flow diagram illustrating a process 100 for extracting 3D information from a 2D image, according to an embodiment of the present invention. In some embodiments, process 100 may begin at 105 with capturing a first image of a sample at a first orientation. For example, by using TEM, electrons may begin on one side of the sample, go through the sample, and land on a detector, which is on the other side of the sample. By doing this, 2D information is received. At 110, a second image of the sample is captured at a second (or different) orientation. In some embodiment, the sample may be tilted with respect to the electron beam. At 115, using the second image, a third dimension of information is then extracted. For example, the third dimension of information is extracted using the mathematical approach defined below.

Experimental Methods

Samples were prepared for TEM analysis by jet electropolishing. TEM may then be performed on a FEI Tecnai T3, which operates at 300 kV.

Tomographic Method—Calculating Z

Tomograms presented and constructed of two images are based on the premise that points in the image become closer or further away from each other as the specimen is tilted. This effect is known as the "parallax". When tilting in the TEM using a single axis, points in the images shift with respect to each other. The amount of shift is related to the position of the point in the 3D space. A point could be where a dislocation intersects either foil surface, a point along a dislocation line, the center of a precipitate or cavity, or along the line where an interface intersects the foil surface. The third dimension of the location of the points is extracted by the following method.

Figure 2:
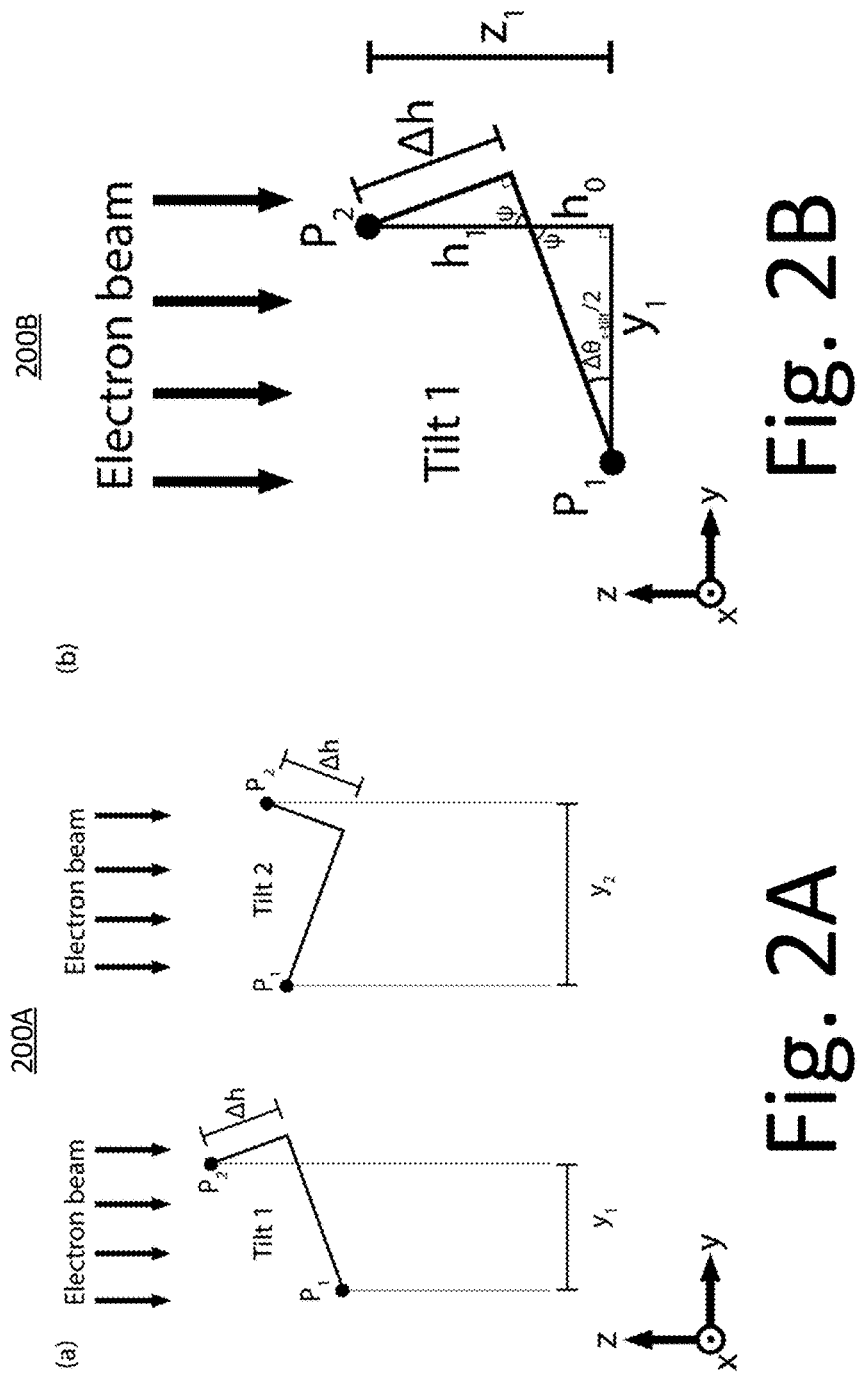
FIG. 2A illustrates a diagram showing the principal of the parallax with respect to embodiments of the present invention.
FIG. 2B illustrates a diagram corresponding to equations (1)-(6), according to an embodiment of the present invention.

3D position information may be extracted from the amount of tilt between two micrographs and the x and y coordinates in each. First, at two values of tilt, the x and y coordinates of each point corresponding to features in the two TEM micrographs are measured. The coordinates in the first and second micrographs are defined by $x_1$ and $y_1$, and $x_2$ and $y_2$, respectively. FIG. 2A illustrates the positions of two points in a TEM foil with respect to the electron beam direction for two different x-axis tilts of the foil. In FIG. 2A, there are two points, $P_1$ and $P_2$. From the diagram shown in FIG. 2A, it should be noted that the distance between $P_1$ and $P_2$ changes in the y-direction after the sample is tilted about the x-axis. $P_1$ will be referred to as the reference point and the coordinates of $P_2$ will be calculated with respect to $P_1$ in certain embodiments. It is known from the parallax concept that $\Delta h$ in FIG. 2A can be determined by equation (1) shown below.

$$\Delta h = \frac{y_2 - y_1}{2*\sin\left(\frac{1}{2}*(\Delta\theta_{x-tilt})\right)} \quad (1)$$

Further manipulations may permit the determination of $z_1$, which corresponds to the distance in the z direction between $P_1$ and $P_2$ at the first tilt frame of reference (tilt 1). The variables for the following equations to determine the coordinates of $P_2$ with respect to $P_1$ are defined in FIG. 2B.

$$z_1 = h_0 + h_1 \quad (2)$$

where $$h_0 = y_1 * \tan\left(\frac{\Delta\theta_{x-tilt}}{2}\right) \quad (3)$$

and $$h_1 = \frac{\Delta h}{\sin(\psi)} = \frac{\Delta h}{\sin\left(90° - \frac{\Delta\theta_{x-tilt}}{2}\right)} \quad (4)$$

such that $$z_1 = y_1 * \tan\left(\frac{\Delta\theta_{x-tilt}}{2}\right) + \frac{\Delta h}{\sin\left(90° - \frac{\Delta\theta_{x-tilt}}{2}\right)} \quad (5)$$

With the measured values of $x_1$ and $y_1$ combined with the calculated $z_1$, the position of $P_2$ with respect to $P_1$ is provided. The reference point $P_1$ has (x,y,z) position of (0,0,0). This process is used individually for multiple points $P_2, P_3, P_4 \ldots$ with respect to the same reference point $P_1$ to create the tomographic model. These positions are in a frame of reference of tilt 1 shown in FIG. 2A with respect to the electron beam.

In other embodiments, Equation (5) may be rewritten as $$z_1 = \frac{y_2}{\sin(\Delta\theta_{x-tilt})} - \frac{y_1}{\tan(\Delta\theta_{x-tilt})} \quad (6)$$

Figure 3:
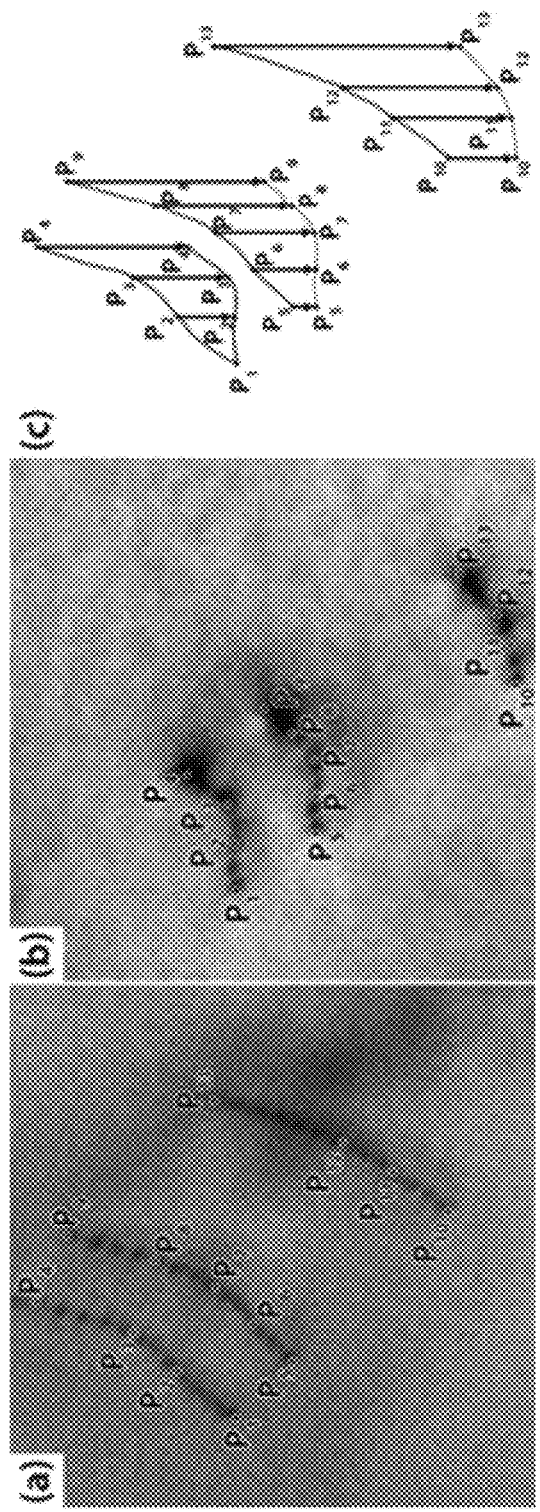
FIG. 3 illustrates images (a)-(c), with images (a) and (b) showing Bright-field TEM micrographs of dislocations observed at x-tilt values of 40.6° and 11.1° respectively, and image (c) showing a position of the points from both (a) and (b) where point $P_1$ is the reference point, according to an embodiment of the present invention.

FIG. 3 illustrates images (a)-(c) showing an example of what is required for calculating coordinates of points along three dislocations, according to an embodiment to the present invention. The three dislocations are viewed at two x-tilts, 40.6° and 11.1°, in images (a) and (b). Image (c) shows how positions along the dislocations in image (a) shift to map onto the same position along the dislocations in image (b). Multiple positions are tracked along the dislocations with respect to the reference point $P_1$. Using the mathematical equations above, the coordinates of each point with respect to $P_1$ may be yielded. If a larger number of points are chosen along the dislocation line, then greater resolution is produced in the model.

In FIG. 3(c), the shift of the points due to tilting the sample is observed by the arrows, which are all in the same direction. The direction of the shift in some cases may be in both the positive and negative direction. The direction of the shift may be determined for each microscope and may be different for different magnifications because of rotations. Finding the direction may be accomplished by overlaying the images such that a point (reference point) is in the same position in the two micrographs and measuring the shift of points where dislocations meet a surface of the foil. In some embodiments, any of the points may be used as a reference point. Knowing the direction of the shift is essential for calculating coordinates of positions on lines such as positions along dislocations in the foil interior, as well as positions along the lines of where interfaces meet a foil surface. By measuring the shift and knowing the tilt, the $z_1$ coordinate may be calculated from equation (5) and combined with the measured $x_1$ and $y_1$ coordinates.

Tomographic Method—Foil Thickness Determination

The calculated coordinates for each point may be manipulated with coordinate transformations to determine the foil thickness. This may be done by two rotations of the coordinates such that the z direction is in the foil thickness direction, i.e., as if the x- and y-tilt of the foil is zero in the microscope. This may provide two advantages. First, the foil thickness is more easily determined as the z-axis and foil thickness are in the same direction, and second, visualizing the data at specific orientations corresponding to tilts in the microscope makes checking the accuracy of the model easier by overlying on images not used to make the model. The two coordinate transformations, one along the x- and one along the y-tilt axis, according to the tilt the first micrograph was captured.

Tomographic Method—Reorienting Coordinates to Align with the Crystallographic Directions Incorporating crystallographic information into the models can be achieved with diffraction spots from diffraction patterns. For example, two diffraction vectors are required and can be from different tilts of the specimen. The direction of each diffraction vector may be determined by subtracting the pixel position of the transmitted beam with that of the diffracted beam and taking z to be zero. The direction of each diffraction vector is then transformed to the zero-tilt orientation such that the diffraction vectors directions are in the same frame of reference as the points of the features when z is in the foil thickness direction. Using two additional coordinate transformations, the coordinates of the calculated positions of features, in the zero-tilt reference frame, can then be in a reference frame such that the x, y and z coordinates of the positions are aligned with the crystallographic directions, i.e. the x-axis is in the [100], the y-axis is in the [010], and the z-axis in the [001] crystallographic directions.

The method used for the results presented here first aligns one of the crystallographic directions, in the zero-tilt reference frame, with a coordinate transformation such that the crystallographic direction is aligned with the x, y and z coordinates, i.e., a [$\bar{1}$11] h, k and l diffraction vector would correspond to the vector [$\bar{1}$11] in the x, y and z coordinate system. A second crystallographic direction, in the zero-tilt reference frame, may then be transformed by the transformation required to align the first diffraction vector. The second crystallographic direction h, k and l might not match its x, y and z coordinates. The second transformation is a rotation about the first crystallographic diffraction vector (after the first coordinate transformation) at the angle required to match the second direction h, k and l to the x, y and z coordinates. Each calculated point and crystallographic direction, in the zero-tilt frame of reference, transformed by the two sequential coordinate transformations resulting in the crystallographic directions aligned with the x, y and z coordinate axis. It is crucial that the indexing of the diffraction vectors is correct.

Result—Dislocations

Figure 4:
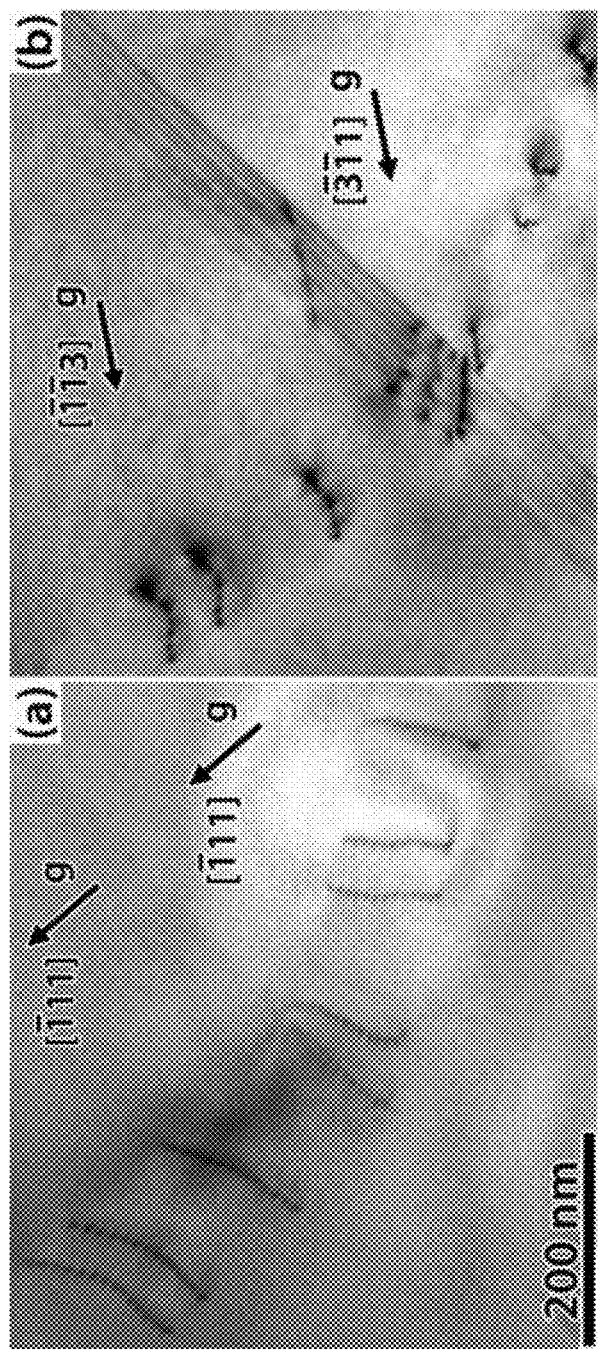
FIG. 4 illustrates Bright-field TEM micrographs (images (a) and (b)) of dislocations in two grains and a twin interface observed at x-tilt values of 40.6° and 11.1°, respectively, according to an embodiment of the present invention.

Dislocations and a twin boundary are shown in images (a) and (b) of FIG. 4 in an Inconel 690 alloy. In FIG. 4, images (a) and (b) are 29.5° apart in tilt. It should also be noted because images (a) and (b) have different diffraction contrast conditions, a model may be created with the same or different diffraction conditions. The diffraction imaging vectors, or g-vectors, for the individual grains in both images are labeled in FIG. 4. The points for calculating the model are along the line of the dislocations as was described above with respect to FIG. 3 except that more points were used in this example. Dislocations were modeled on both sides of the interface as well as in the interface.

Figure 5:
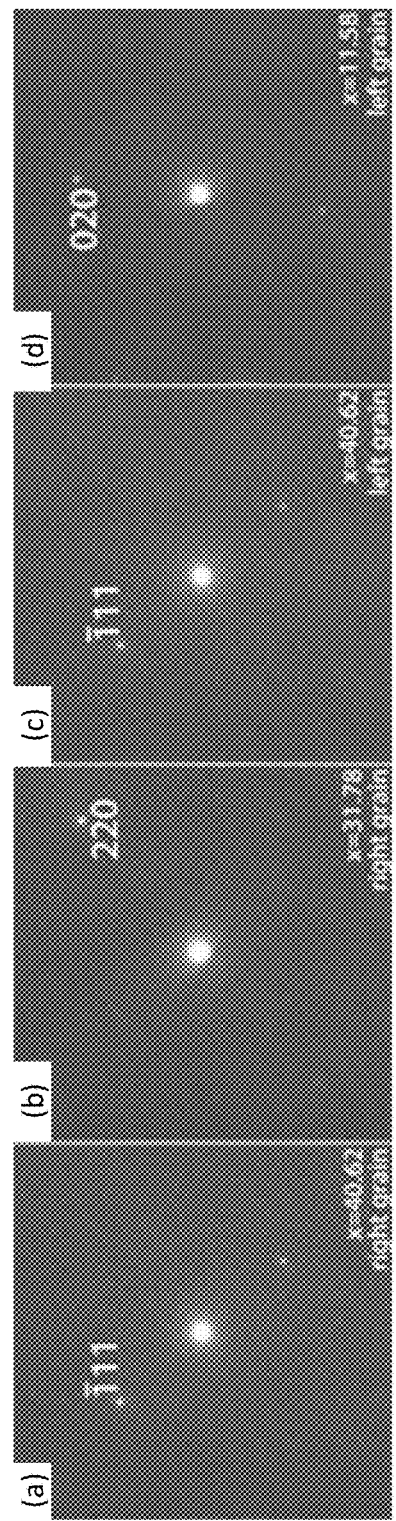
FIG. 5 illustrates select area diffraction patterns in images (a)-(d) from the grains shown in images (a)-(b) of FIG. 4, according to an embodiment of the present invention.

Crystallographic directions were incorporated from the four diffraction patterns, presented in images (a)-(d) of FIG. 5. The diffraction patterns from images (a) and (b) of FIG. 5 are from the grain on the right, while images (c) and (d) of FIG. 5 are from the grain on the left. The value of x-tilt for each diffraction pattern was captured and is also marked in FIG. 5. It should be noted that none of the diffraction information used was from a zone axis pattern, though a zone axis pattern would support all the diffraction information to add the crystallographic directions. Only x-tilt was used for this experiment exhibiting the application to experiments such as in situ straining where only one axis of tilt is available.

Using the incorporated crystallographic information, it was determined that the dislocations to the left of the twin boundary slip on the $(\bar{1}\bar{1}1)_M$ plane and have line directions near $[101]_M$, while those on the right side of the interface slip on the $(111)_T$ plane and have line directions near $[\bar{1}2\bar{1}]_T$. Subscripts M and T denote matrix and twin, and were assigned to the left and right grains, respectively. The interface plane normal was also determined and is the $(\bar{1}11)_{T,M}$ plane.

Figure 6:
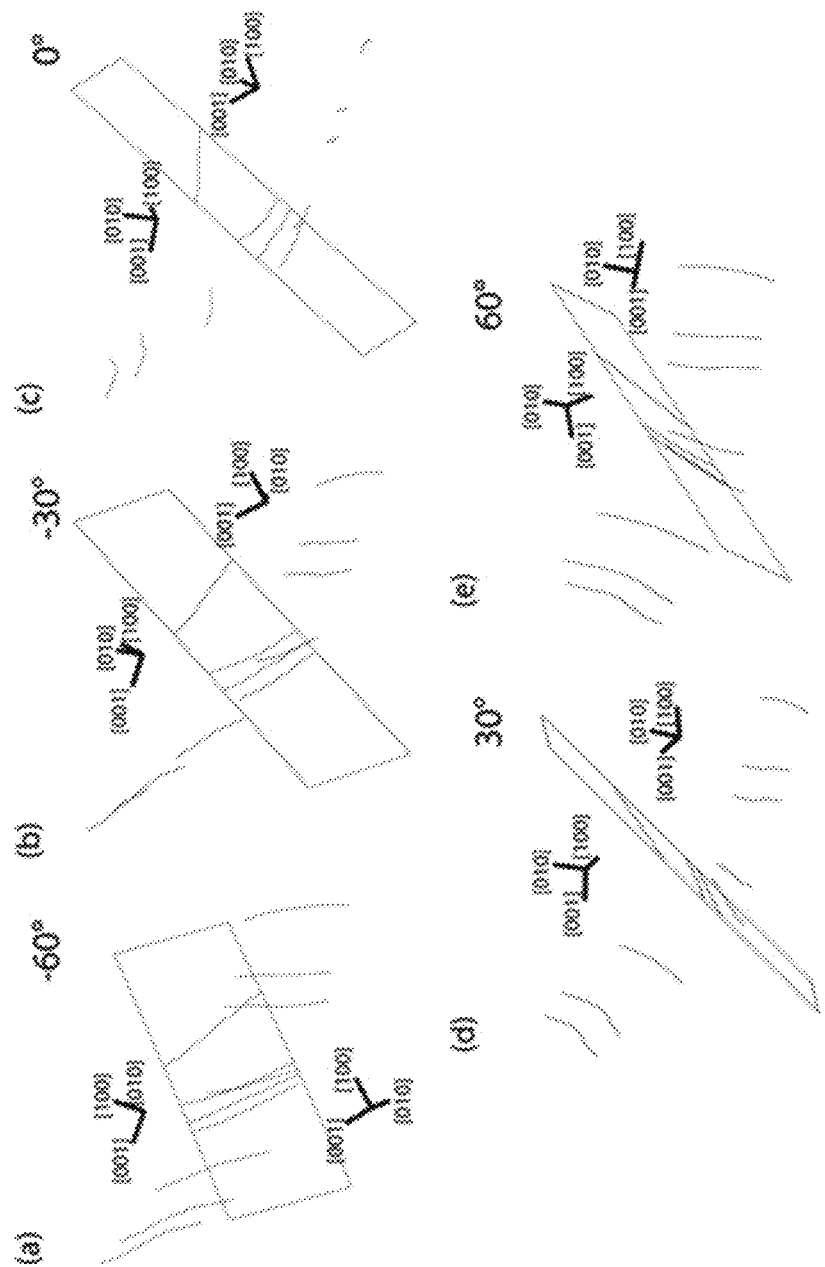
FIG. 6 illustrates a 3D model including crystallographic directions from FIGS. 4 and 5, according to an embodiment of the present invention.

FIG. 6 illustrates a 3D model including crystallographic directions from FIGS. 4 and 5, according to an embodiment of the present invention. In FIG. 6, dislocations, the interface and the [1,0,0], [0,1,0], and [0,0,1] crystalline directions are presented. Plotting of the calculated data was performed using the Python Mayavi package.

Figure 7:
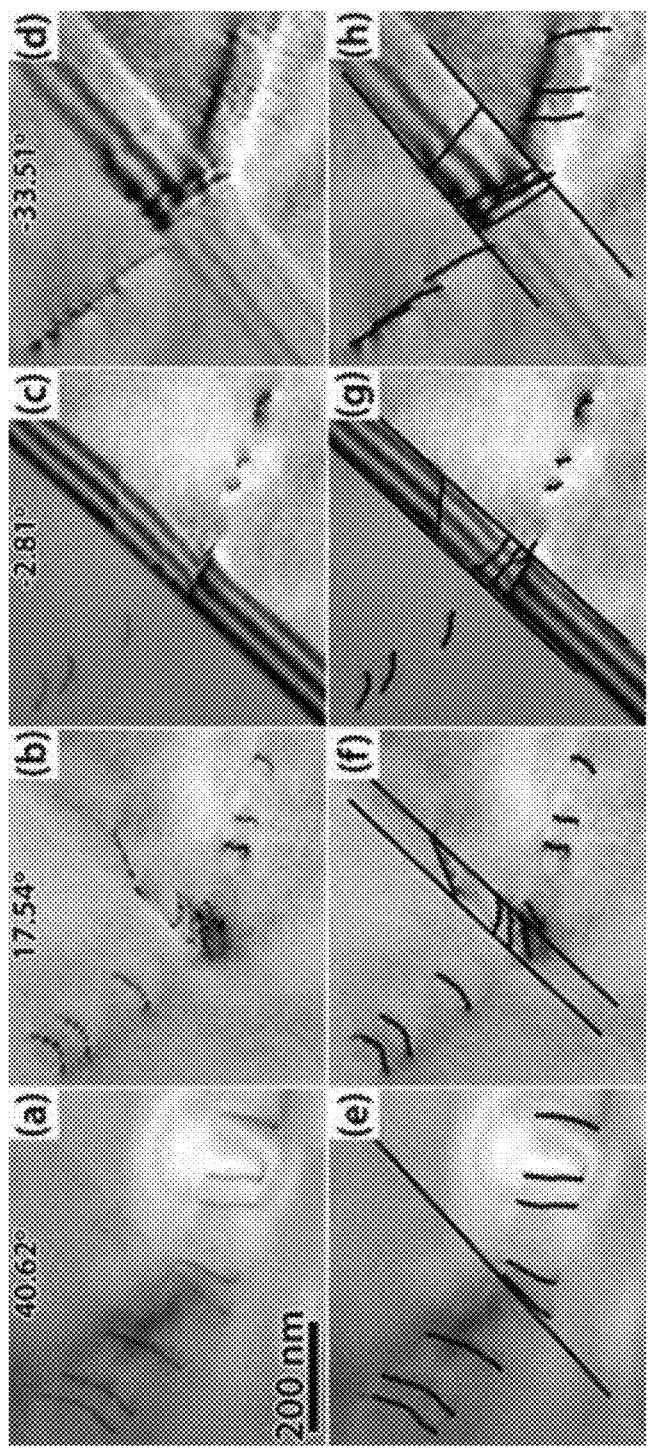
FIG. 7 illustrates TEM images (a)-(h) captured at a range of tilts from 40.62° to −33.51°, according to an embodiment of the present invention.

Checking the accuracy of the positions may be done by overlaying the model on images captured at various tilts. To ensure the check is correct, the position should undergo two coordinate transformations, one for x-axis tilt and one for y-axis tilt, to place the z-axis in the beam direction and the x- and y-axis such that they correspond to a foil at zero tilt. By doing this, the viewing orientation with the visualization method of choice may be matched with the tilt of the various images used for checking. FIG. 7 illustrates images (a)-(h) captured at a range of tilts from 40.62° to −33.51°, according to an embodiment of the present invention. In this embodiment, images (a)-(d) are bright-field transmission electron micrographs of the region of the model captured at various orientations (or tilts) without the 3D model overlaid. Images (e)-(h) are the images from (a)-(d) with the 3D model overlaid on the images to show the good correlation of the model to the microstructure.

Figure 8:
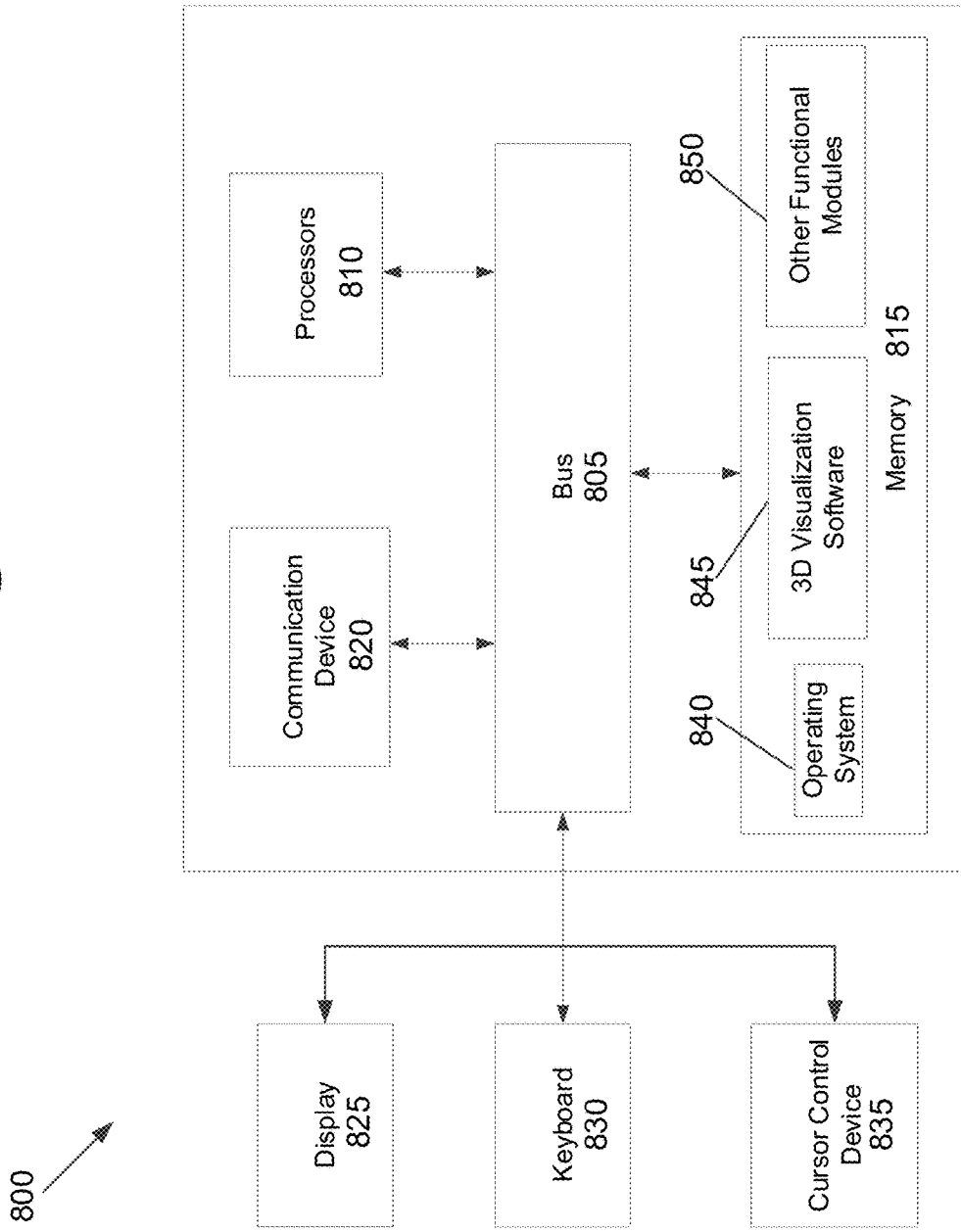
FIG. 8 is a block diagram illustrating a computing system configured to run a 3D visualization software according to an embodiment of the present invention.

FIG. 8 is a block diagram illustrating a computing system configured to run a 3D visualization software, according to an embodiment of the present invention. Computing system 800 includes a bus 805 or other communication mechanism for communicating information, and processors 810 coupled to bus 805 for processing information. Processor(s) 810 include at least one CPU and at least one GPU.

Processors 810 may also have multiple processing cores, and at least some of the cores may be configured to perform specific functions. Multi-parallel processing may be used in some embodiments. Computing system 800 further includes a memory 815 for storing information and instructions to be executed by processors 810. Memory 815 can be comprised of any combination of random access memory (RAM), read only memory (ROM), flash memory, cache, static storage such as a magnetic or optical disk, or any other types of non-transitory computer-readable media or combinations thereof. Additionally, computing system 800 includes a communication device 820, such as a transceiver and antenna, to wirelessly provide access to a communications network.

Non-transitory computer-readable media may be any available media that can be accessed by processors 810 and may include both volatile and non-volatile media, removable and non-removable media, and communication media. Communication media may include computer-readable instructions, data structures, program modules or other data in a modulated data signal such as a carrier wave or other transport mechanism and includes any information delivery media.

Processors 810 are further coupled via bus 805 to a display 825, such as a Liquid Crystal Display (LCD), for displaying information to a user. A keyboard 830 and a cursor control device 835, such as a computer mouse, are further coupled to bus 805 to enable a user to interface with computing system. However, in certain embodiments such as those for mobile computing implementations, a physical keyboard and mouse may not be present, and the user may interact with the device solely through display 825 and/or a touchpad (not shown). Any type and combination of input devices may be used as a matter of design choice.

Memory 815 stores software modules that provide functionality when executed by processors 810. The modules include an operating system 840 for computing system 800. The modules further include a 3D visualization module 845 that is configured to perform 3D image generation by employing any of the approaches discussed herein or derivatives thereof. Computing system 800 may include one or more additional functional modules 850 that include additional functionality.

One skilled in the art will appreciate that a "system" could be embodied as an embedded computing system, a personal computer, a server, a console, a personal digital assistant (PDA), a cell phone, a tablet computing device, or any other suitable computing device, or combination of devices. Presenting the above-described functions as being performed by a "system" is not intended to limit the scope of the present invention in any way but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, be comprised of one or more physical or logical blocks of computer instructions that may, for instance, be organized as an object, procedure, or function. Nevertheless, the executables of an identified module need not be physically located together but may be comprised of disparate instructions stored in different locations which, when joined logically together, comprise the module and achieve the stated purpose for the module. Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

The process steps performed in FIG. 1 may be performed by a computer program, encoding instructions for the nonlinear adaptive processor to perform at least the process described in FIG. 1, in accordance with embodiments of the present invention. The computer program may be embodied on a non-transitory computer-readable medium. The computer-readable medium may be, but is not limited to, a hard disk drive, a flash device, a random access memory, a tape, or any other such medium used to store data. The computer program may include encoded instructions for controlling the nonlinear adaptive processor to implement the process described in FIG. 1, which may also be stored on the computer-readable medium.

The computer program can be implemented in hardware, software, or a hybrid implementation. The computer program can be composed of modules that are in operative communication with one another, and which are designed to pass information or instructions to display. The computer program can be configured to operate on a general purpose computer, or an ASIC.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A computer-implemented method for extracting three-dimensional (3D) data to create a 3D representation from two two-dimensional (2D) images, the method comprising:
   capturing a first image of a sample at a first orientation;
   capturing a second image at a second or different orientation from that of the first orientation;
   extracting 3D information using the first captured image and the second captured image to create a 3D representation;
   incorporating crystallographic information into the 3D representation, wherein the incorporating of the crystallographic information comprises
      determining a direction of each diffraction vector by subtracting pixel position of a transmitted beam with that of a diffracted beam and taking a z-direction to be zero;
      transforming the direction of each diffraction vector to a zero-tilt orientation such that each diffraction vector direction is in a same frame of reference as points of features when the z-direction is in a direction of the foil thickness; and
   using coordinate transformations to align x, y, and z coordinates of the positions with crystallographic directions.

2. The method of claim 1, wherein the capturing of the first image comprises
   using a transmission electron microscopy (TEM) to emit electrons from one side of the sample through an opposite side of the sample such that the electrons land on the detector.

3. The method of claim 1, wherein the capturing of the second image comprises
   tilting the sample with respect to an electron beam emitted from a transmission electron microscopy (TEM) to capture the second image.

4. The method of claim 1, wherein the extracting of the 3D information comprises
   extracting 3D position information from an amount of tilt between the captured first image and the second captured image and x and y coordinates in each of the first image and the second image.

5. The method of claim 4, wherein the extracting of the 3D position information comprises
   at two values of the tilt, measuring the x and y coordinates of each point corresponding to features in the captured first image and the captured second image.

6. The method of claim 5, wherein the extracting of the 3D position information comprises
   calculating a position of the second through last point individually with respect to the first point using the measured x and y coordinates with a calculated z coordinate.

7. The method of claim 1, further comprising:
   manipulating calculated coordinates for each point with coordinate transformations to determine a foil thickness, wherein the manipulating comprises
   performing two rotations of the calculated coordinates, such that a z-direction is in a direction of the foil thickness and represents a zero-tilt frame of reference.

8. A non-transitory computer-readable medium comprising a computer program configured to extract 3D information from two 2D images, wherein the computer program, when executed by at least one processor, is configured to
   capture a first image of a sample at a first orientation;
   capture a second image at a second or different orientation from that of the first orientation;
   extract 3D information using the first captured image and the second captured image to create a 3D representation from the 2D images;
   index two diffraction vectors;

determine a direction of each diffraction vector by subtracting pixel position of a transmitted beam with that of a diffracted beam and taking a z-direction to be zero;
transform the direction of each diffraction vector to a zero-tilt orientation such that each diffraction vector direction is in a same frame of reference as points of features is the zero-tilt frame of reference; and
use coordinate transformations to align x, y, and z coordinates of the positions with crystallographic directions.

9. The non-transitory computer-readable medium of claim 8, wherein the computer program is further configured to
use a transmission electron microscopy (TEM) to emit electrons from one side of the sample through an opposite side of the sample such that the electrons land on the detector.

10. The non-transitory computer-readable medium of claim 8, wherein the computer program is further configured to
tilt the sample with respect to an electron beam emitted from a transmission electron microscopy (TEM) to capture the second image.

11. The non-transitory computer-readable medium of claim 8, wherein the computer program is further configured to
extract 3D position information from an amount of tilt between the captured first image and the second captured image and x and y coordinates in each of the first image and the second image.

12. The non-transitory computer-readable medium of claim 11, wherein the computer program is further configured to
at two values of the tilt, measure the x and y coordinates of each point corresponding to features in the captured first image and the captured second image.

13. The non-transitory computer-readable medium of claim 12, wherein the computer program is further configured to
calculate a position of the second through last point individually with respect to the first point using the measured x and y coordinates with a calculated z coordinate.

14. The non-transitory computer-readable medium of claim 8, wherein the computer program is further configured to
manipulate calculated coordinates for each point with coordinate transformations to determine a foil thickness, wherein the manipulating comprises
performing two rotations of the calculated coordinates, such that a z-direction is in a direction of the foil thickness and corresponds to a zero-tilt sample orientation in the microscope.

15. An apparatus configured to extract three-dimensional (3D) data to create a 3D representation from a two-dimensional (2D) image, the method comprising:
at least one processor;
memory comprising a set of instructions, wherein
the set of instructions are configured to cause the processor to
capture a first image of a sample at a first orientation;
capture a second image at a second or different orientation from that of the first orientation;
extract 3D information using the first captured image and the second captured image to create a 3D representation from the 2D images;
index two diffraction vectors;
determine a direction of each diffraction vector by subtracting pixel position of a transmitted beam with that of a diffracted beam and taking a z-direction to be zero;
transform the direction of each diffraction vector to a zero-tilt orientation such that each diffraction vector direction is in a same frame of reference as points of features is the zero-tilt frame of reference; and
use coordinate transformations to align x, y, and z coordinates of the positions with crystallographic directions.

16. The apparatus of claim 15, wherein the set of instructions are further configured to cause the processor to use a transmission electron microscopy (TEM) to emit electrons from one side of the sample through an opposite side of the sample such that the electrons land on the detector.

17. The method of claim 15, wherein the set of instructions are further configured to cause the processor to tilt the sample with respect to an electron beam emitted from a transmission electron microscopy (TEM) to capture the second image.

18. The method of claim 15, wherein the set of instructions are further configured to cause the processor extract 3D position information from an amount of tilt between the captured first image and the second captured image and x and y coordinates in each of the first image and the second image.

* * * * *